(12) United States Patent
Aumaitre

(10) Patent No.: US 9,539,045 B2
(45) Date of Patent: Jan. 10, 2017

(54) CRYOGENIC DEVICE FOR SURGICAL USE

(75) Inventor: Olivier Aumaitre, Montreuil (FR)

(73) Assignee: PHAKOS, Montreuil (FR)

( * ) Notice: Subject to any disclaimer, the term of this patent is extended or adjusted under 35 U.S.C. 154(b) by 678 days.

(21) Appl. No.: 12/602,326

(22) PCT Filed: May 27, 2008

(86) PCT No.: PCT/FR2008/000720
§ 371 (c)(1),
(2), (4) Date: Feb. 16, 2010

(87) PCT Pub. No.: WO2009/004156
PCT Pub. Date: Jan. 8, 2009

(65) Prior Publication Data
US 2010/0137853 A1 Jun. 3, 2010

(30) Foreign Application Priority Data

May 31, 2007 (FR) ...................................... 07 55370

(51) Int. Cl.
*A61B 18/02* (2006.01)
*A61B 18/00* (2006.01)

(52) U.S. Cl.
CPC ...... *A61B 18/02* (2013.01); *A61B 2018/00023* (2013.01); *A61B 2018/0262* (2013.01)

(58) Field of Classification Search
CPC ........... A61B 2018/00017; A61B 2018/00023; A61B 2018/00321; A61B 2018/0262; A61B 18/02
USPC ....................... 606/20–26; 607/104, 105, 114
See application file for complete search history.

(56) References Cited

U.S. PATENT DOCUMENTS

| | | | |
|---|---|---|---|
| 3,421,508 A | | 1/1969 | Nestrock |
| 3,696,813 A | * | 10/1972 | Wallach ........................ 606/26 |
| 3,971,383 A | * | 7/1976 | van Gerven ................... 606/23 |
| 4,029,102 A | * | 6/1977 | Barger ............................ 606/23 |
| 5,254,116 A | * | 10/1993 | Baust et al. .................... 606/23 |
| 5,324,286 A | * | 6/1994 | Fowle ............................. 606/23 |
| 5,423,807 A | * | 6/1995 | Milder ............................ 606/20 |
| 5,520,682 A | * | 5/1996 | Baust et al. .................... 606/24 |
| 5,573,532 A | * | 11/1996 | Chang et al. .................. 606/26 |
| 6,235,048 B1 | * | 5/2001 | Dobak, III .................... 607/104 |
| 6,551,309 B1 | | 4/2003 | LePivert |
| 6,926,711 B2 | * | 8/2005 | Lentz et al. ................... 606/21 |
| 8,353,942 B2 | * | 1/2013 | Merrill ......................... 607/105 |
| 2002/0062122 A1 | * | 5/2002 | Lehmann et al. ............. 606/23 |
| 2002/0120258 A1 | * | 8/2002 | Lalonde ......................... 606/23 |
| 2004/0073203 A1 | * | 4/2004 | Yu et al. ........................ 606/21 |

(Continued)

FOREIGN PATENT DOCUMENTS

| | | |
|---|---|---|
| WO | WO 99/37226 | 7/1999 |
| WO | WO 00/32126 | 6/2000 |

*Primary Examiner* — Jocelyn D Ram
(74) *Attorney, Agent, or Firm* — Cantor Colburn LLP

(57) ABSTRACT

The disclosure relates to a cryogenic device for surgical use, which can be used to cool an area of the body and includes: a cryogenic gas supply conduit and a discharge conduit, an end piece comprising a metal tip intended to be brought into contact with the area to be cooled and a gas release chamber and a gas injection nozzle connected to the supply conduit at the one end and opening into the chamber in the direction of the metal tip at the other end. The supply conduit and the discharge conduit are formed in a common flexible extruded tube that is inserted into the end piece.

13 Claims, 3 Drawing Sheets

(56) References Cited

U.S. PATENT DOCUMENTS

| | | | |
|---|---|---|---|
| 2004/0143312 A1* | 7/2004 | Samson et al. | 607/105 |
| 2005/0010200 A1* | 1/2005 | Damasco et al. | 606/21 |
| 2005/0043724 A1* | 2/2005 | Ryba | 606/23 |
| 2005/0228368 A1* | 10/2005 | Yon et al. | 606/21 |
| 2006/0004350 A1* | 1/2006 | Ryba | 606/21 |
| 2007/0049912 A1* | 3/2007 | Damasco et al. | 606/21 |
| 2008/0065179 A1* | 3/2008 | Yon et al. | 607/105 |
| 2008/0119836 A1* | 5/2008 | Littrup et al. | 606/21 |
| 2013/0035678 A1* | 2/2013 | Sick et al. | 606/20 |
| 2013/0090639 A1* | 4/2013 | Atias et al. | 606/23 |

* cited by examiner

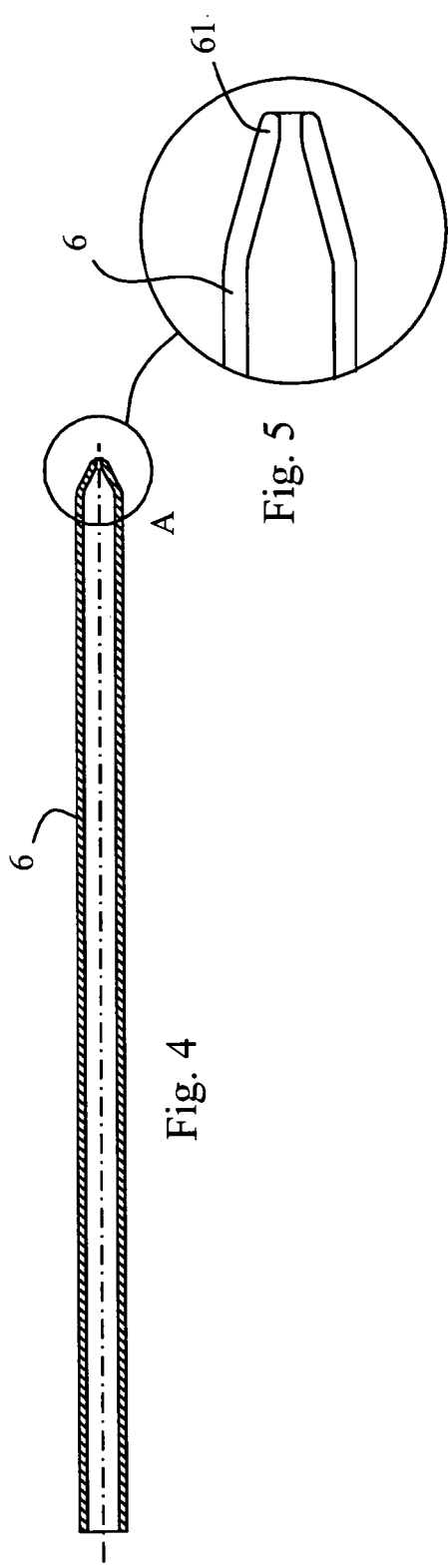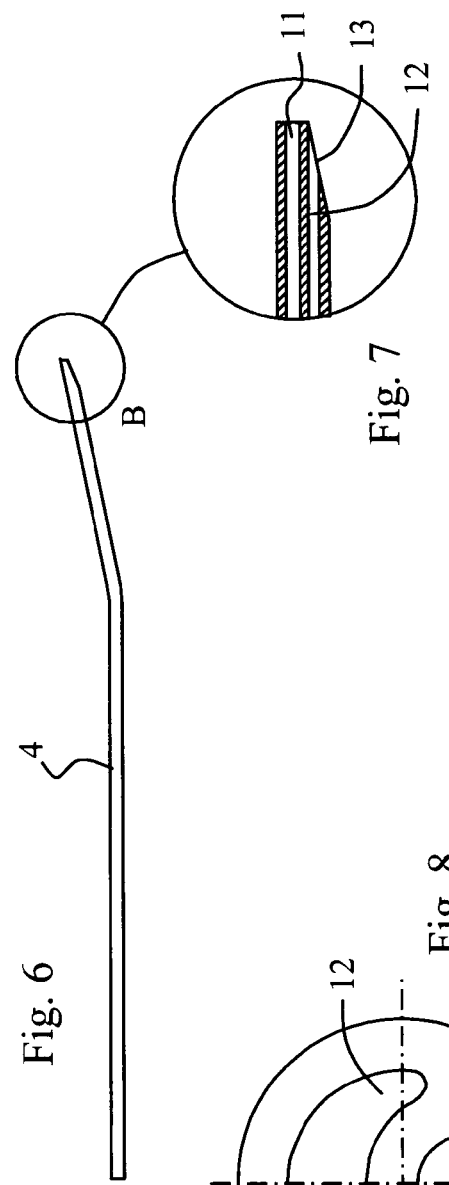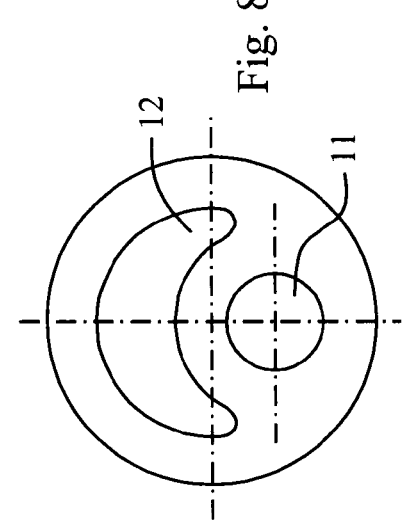

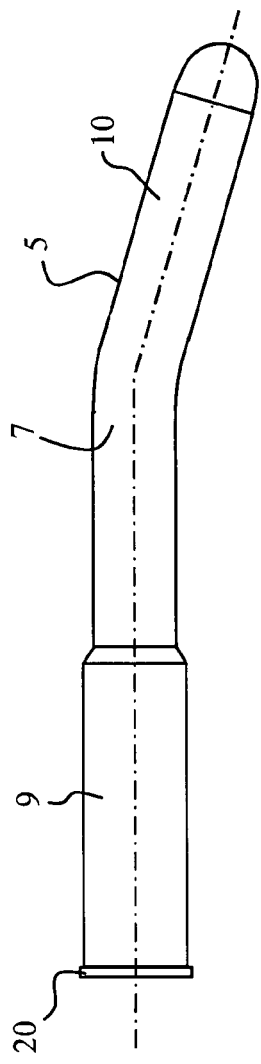
Fig. 9
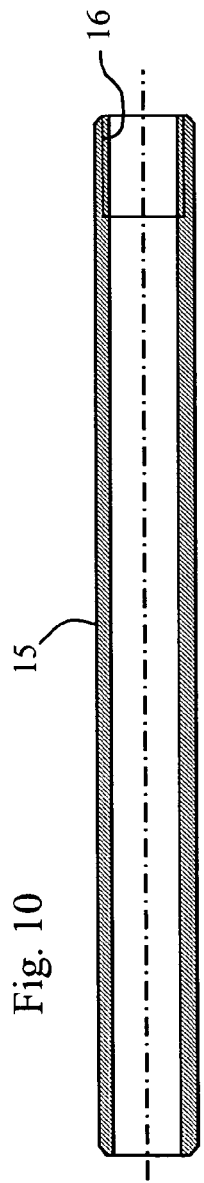
Fig. 10
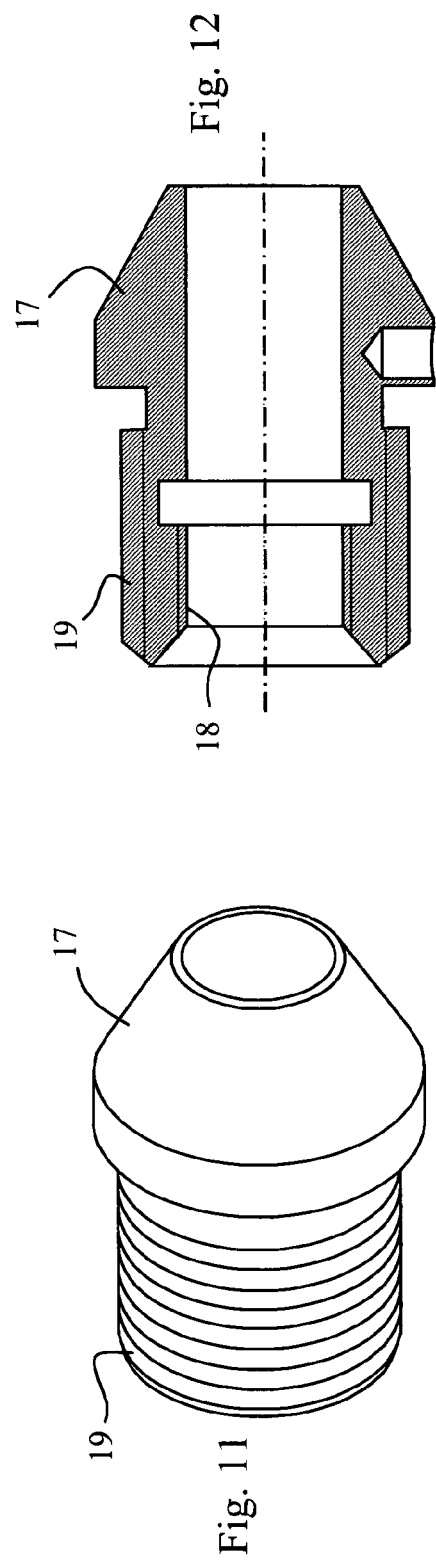
Fig. 11
Fig. 12

CRYOGENIC DEVICE FOR SURGICAL USE

CROSS-REFERENCE TO RELATED APPLICATIONS

This application is a National Phase Entry of International Application No. PCT/FR2008/000720, filed on May 27, 2008, which claims priority to French Application 0755370, filed on May 31, 2007, both of which are incorporated by reference herein.

BACKGROUND AND SUMMARY

The invention relates to a cryogenic device for medical applications. The invention more particularly relates to cryogenic device to be used once for ophthalmologic surgery.

In the prior art, cryogenic devices for medical applications are known. Such devices are more particularly used in the field of ophthalmologic cryosurgery and more particularly to treat retinal detachment by generating a cold point making it possible to create an adhesive scar by burning tissues between the retina and the choroid. The devices of the prior art are generally composed of a supply conduit connected to a source of cryogenic gas (nitrous oxide, carbon dioxide), of a conduit for discharging said gas, of a metal tip intended to be brought into contact with the area to be cooled and provided with a gas release chamber and a gas injection nozzle which supplies the gas from the supply conduit to the release chamber.

Manufacturing the devices of the prior art is expensive, takes time and is difficult more particularly because of the number of parts which compose the same. Consequently, in order to limit the costs, the devices are generally intended to be used many times. This imposes that such devices are capable of supporting sterilisation conditions at the hospital or according to international standards, sterilisation is obtained by staying in an autoclave at 125° C. for 10 minutes. Because the French standard is still more restricting since it requires a 20 minutes' stay at 134° C. Such constraints imply technological choices which make the devices still more complex and more expensive. In addition, sterilised devices using this procedure undergo deteriorations imposing frequent and costly maintenance actions when and as they are sterilised.

In order to remedy such drawbacks, the invention aims at providing a cryogenic device to be used once which can be reliable and the manufacturing of which is simple and less expensive. Another object of the invention is also to provide a light ergonomic, sterile and secured cryogenic device.

For this purpose and according to a first aspect, the invention provides a cryogenic device for surgical use making it possible to cool an area of the body including:
- an end piece including a metal tip intended to be brought into contact with the area to be cooled and a gas release chamber;
- a conduit for supplying the chamber with cryogenic gas; and
- a conduit for discharging the cryogenic gas from the chamber; the supply conduit and the discharge conduit being formed in a common flexible extruded tube, one end of which is inserted into the end piece.

Then, the number of parts composing the device is limited. In addition, the mounting operations are simplified, since the tube containing both supply and discharge conduits is directly inserted into the end piece.

Advantageously, the end piece is made integral with one end of the flexible tube using gluing means. Then, the number of parts is limited by the utilisation of glue and the mounting is particularly simple. Of course using glue is possible only if the probe is sterilised at a low temperature. In practice, low temperature sterilisation, for example using 45° ethylene oxide, requires extractors which are not available in hospitals and it is thus mainly performed under industrial conditions. As a matter of fact, an attachment using a simple gluing step can be considered only because the mounting of the device is much simplified by the utilisation of a two-conduit unique tube; and thus the manufacturing cost can be globally reduced so much so that a one-time use is economically justified.

In one embodiment, the free end of the flexible tube inserted into the end piece is threaded so as to create a roughness at the gluing interface between the end piece and the flexible tube. Advantageously, the supply conduit has a section which is smaller that of the discharge conduit. In one embodiment, the supply conduit has substantially the shape of a crescent and the end of the support conduit is bevelled. Advantageously, the injection nozzle is inserted into the supply conduit. Preferably, the injection nozzle has a conical injection tip.

In one embodiment of the invention, the cryogenic device includes a nut provided with an internal thread and an external thread, a handle provided with the thread cooperating with the external thread of the nut, the end of the flexible tube being provided with a thread cooperating with the internal thread of the nut. Advantageously, the cryogenic device includes an isolating sleeve covering a portion of the end piece. In practice, the supply conduit is connected to a source of pressurised cryogenic gas. The discharge conduit is connected to a silencer discharging gas towards the outside.

BRIEF DESCRIPTION OF DRAWINGS

Other objects and advantages of the invention will appear while reading the following description and referring to the appended drawings, wherein:

FIG. 4 is a schematic sectional view of a gas injection nozzle;

FIG. 5 is a detailed view of the area A in FIG. 4;

FIG. 6 is a schematic view of the flexible extruded tube according to the invention;

FIG. 7 is a detailed longitudinal sectional view of the area B in FIG. 6;

FIG. 8 is a transversal sectional view of the flexible extruded tube;

FIG. 9 shows the metal tip;

FIG. 10 is a longitudinal sectional view of the handle of the device according to the invention;

FIG. 11 is a perspective view of the nut; and

FIG. 12 is a longitudinal sectional view of the nut of FIG. 11.

DETAILED DESCRIPTION

Figure 1:
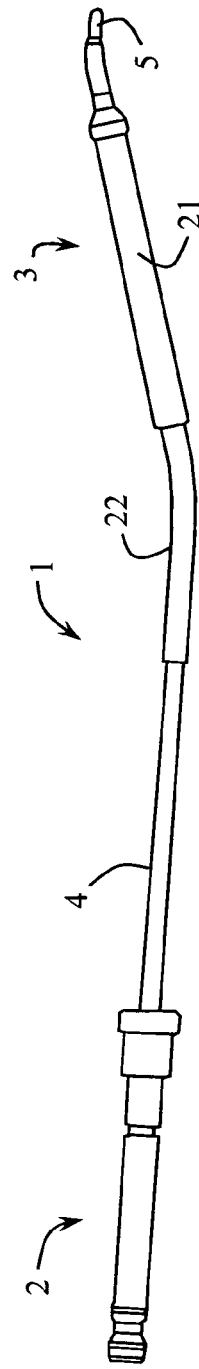
FIG. 1 is a schematic view of a cryogenic device according to the invention.
Figure 2:
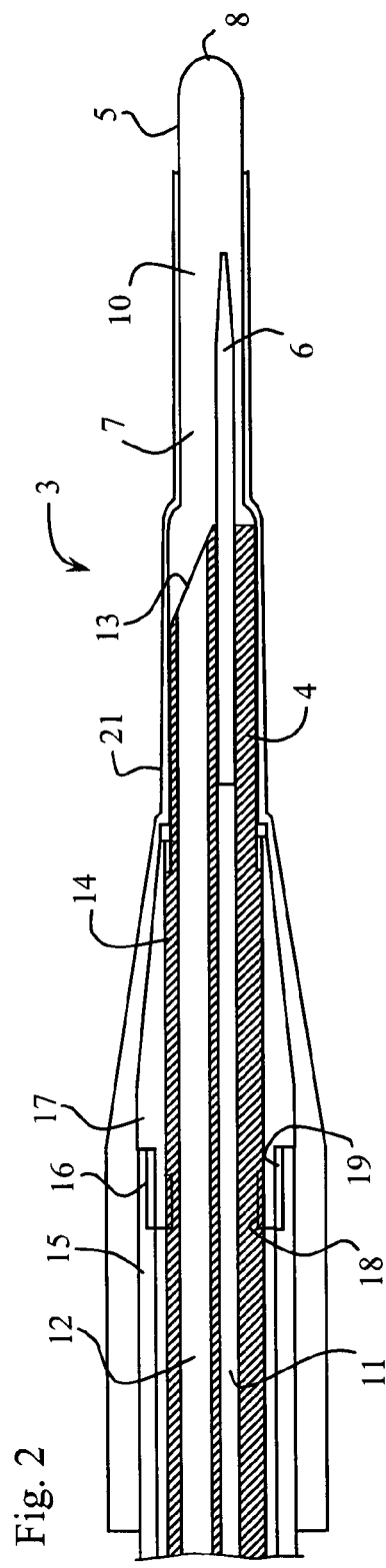
FIG. 2 is a schematic sectional view of the end of the probe intended to be brought into contact with the area of the body to be cooled in the device of FIG. 1.

FIG. 1 shows a cryogenic device 1 according to the invention including a connector 2 intended to be coupled to a liquefied gas tank release valve (nitrous oxide or carbon dioxide) on the one hand, a probe or cryoextractor 3 on the other hand and a flexible tube 4 for transporting the cryogenic fluid connecting the connector 2 to the cryoextractor 3. The cryoextractor 3 shown in FIG. 2 includes a hollow end piece 5, the end of which is intended to be brought into contact with the area to be cooled and an injection nozzle 6 opening into the chamber 7 of the end piece 5 and spraying the cryogenic gas against the end 8 of the cryoextractor 3. Thus, the cryogenic gas cools the walls of the end piece 5 at the end 8 which will be applied onto the tissues to freeze them locally at a temperature lower than −50° C. and preferably of the order of −65° C. to −90° C.

The end piece 5 shown in FIG. 9 is made of a metallic material such as stainless steel, and the walls thereof form a gas release chamber 7 composed of a large section counterboring 9 extended by a canula 10. Advantageously, in order to increase the ergonomy of the device, the end of the end piece 5 is slightly curved. In addition, it should be noted that the end piece 5 is obtained by successive punching operations. Thus, the walls of the end piece 5 have a homogenous thickness so as to reduce the risks of explosion.

The flexible tube 4 shown in FIG. 6 is an extruded tube provided with a supply conduit 11 and a discharge conduit 12 for a cryogenic gas. The end of the flexible tube 4 is inserted into the end piece 5 and closes the end of the end piece 5 so as to provide the sealing of the cryoextractor 3. The end piece 5 is made integral with the flexible tube 4 by gluing. Advantageously, to provide a reliable attachment between the tube 4 and the end piece 5, the free end of the tube 4, which is inserted into the end piece 5, is threaded so as to create a roughness at the gluing interface between the end piece 5 and the tube 4. The glue used may more particularly be cyanolite glue.

The supply 11 and discharge 12 conduits shown in FIGS. 7 and 8 have different shapes and sections. The supply conduit 11 has a substantially cylindrical shape and has a section which is smaller than that of the discharge conduit 12 so as to keep the gas under pressure prior to its being injected into the release chamber 7. On the contrary, in order to keep the release chamber 7 under negative pressure, the section of the discharge conduit 12 is necessarily larger so as to allow the discharge of the gas which has released into said chamber 7. Advantageously, in order to optimise the section of the discharge conduit 12, as a function of the section of the tube 4, the discharge conduit 12 substantially has the shape of a crescent. In addition, the concavity of the crescent is oriented towards the supply conduit 11.

In addition, in order to increase the section of the discharge conduit 12 at the end 13 thereof, the section of the discharge conduit is preferably bevelled (refer to FIG. 7). Advantageously, the tube 4 is made in a polyamide synthetic fibre such as Rilsan® having a very good resistance to wear, shocks and vibrations. In addition, the tube 4 further has a protective external sheath 14 made of PVC. The end of the tube 4 is deprived of the sheath 14 which does not go into the end piece 5. In one embodiment, the length of the tube is between 1.5 and 2.5 meters and preferably of the order of 2 meters so as to give a greater freedom of movement to the operator with respect to the source of gas.

The nozzle 6 shown in a detailed way in FIGS. 4 and 5 is inserted into the supply conduit 11. The nozzle 6 has an injection cone 61 shown in FIG. 5 at the free end thereof, making it possible to vaporize the gas inside the canula 10, against the end 8 of the end piece 5. In one embodiment of the invention, the nozzle 6 is made of stainless steel.

In order to make it possible to handle the cryoextractor, the device is provided with a handle 15 shown in FIG. 10, the distal end of which is provided with a thread 16 cooperating with a nut 17. Preferably, the handle 15 is made of an isolating material such as aluminium. The nut 17 is mounted on the end piece 5 and abuts against a collar 20 formed by the end wall of the end piece 5 protruding towards the outside. The nut 17 has threaded internal wall 18 and external wall 19. The external wall 19 cooperates with the thread 16 of the handle 15 so as to make both elements in one piece, whereas the internal wall 18 is screwed on a thread formed at the end of the sheath 14 of the flexible tube 4, so as to make the nut 17 integral with the tube 4. In one embodiment, the nut 17 is made of stainless steel.

Preferably, the cryoextractor 3 is also provided with a protection sleeve 21 wrapping and isolating a part of the end piece 5, the nut 17 and the end of the handle 15. The sleeve 21 is for example made of silicon and makes it possible to more particularly protect the side walls of the end piece 5 which are also cooled and could thus undesirably adhere to tissues. In one preferred embodiment of the invention, the device 1 is provided with a curved rigid tube 22 made of polycarbonate, making it possible to impart a curve to the end of the flexible tube 4, so as to improve the ergonomy of the device 1. This embodiment also makes it possible to go beyond the microscope used during a surgical operation.

Figure 3:
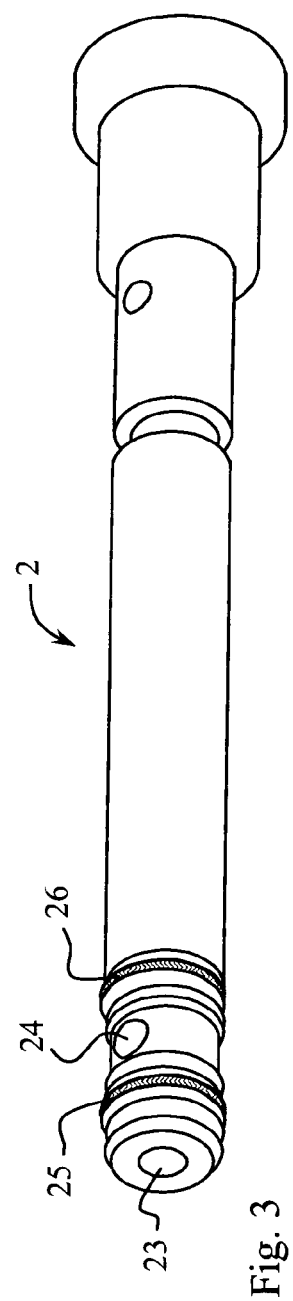
FIG. 3 is a schematic view of a connector according to one embodiment of the invention.

In the embodiment shown in FIG. 3, the connector 2 is provided with a proximal orifice 23 making it possible to introduce gas into the supply conduit and a side orifice 24 for discharging gas. The tube 4 is also made integral with the connector 2 using cyanolite glue. In order to enable a side discharge of gas, the end of the discharge conduit is closed with glue, whereas a side orifice, not shown, is formed in the discharge conduit 12 and positioned in a matching position with the side orifice 24.

In addition, the connector 2 is provided with two O-rings 25, 26 positioned on either side of the side orifice 24. In operation, the side orifice 24 is connected to a silencer enabling the release of gas into the atmosphere. The proximal orifice 23 is connected to a liquefied gas tank (nitrous or carbon dioxide) through a release valve.

It should be noted that all the materials used must be biocompatible so as to make it possible to use the device under surgical conditions. In addition, the devices according to the invention are previously sterilised. Advantageously, the sterilisation is a sterilisation with 45° ethylene oxide. This sterilisation is carried out according to industrial standards and requires extractors which are usually not available in hospitals. This type of sterilisation is less affecting the device 1 and makes it possible to use gluing means such as cyanolite glue. When they are sterilised, the devices 1 are packed in sterile packing and they are ready to be transferred to the place of the surgical operation.

The invention has been described hereabove as an example. It should be understood that the persons skilled in the art can make various modifications of the embodiments of the invention without leaving the scope of the invention.

The invention claimed is:

1. A cryogenic device for a surgical use making it possible to freeze an area of a human body at a temperature lower than −50° C., the cryogenic device comprising:
    an end piece including a metal tip configured to be brought into contact with the area to be frozen and a cryogenic gas release chamber;
    a flexible tube externally delimited by an outer wall, an end of which is inserted into the end piece, and containing:

a discharge conduit directly communicating with the cryogenic gas release chamber for discharging a cryogenic gas directly from the cryogenic gas release chamber, and a supply conduit for supplying the gas release chamber with the cryogenic gas, the supply conduit being distinct from the discharge conduit so that the supply conduit communicates with the discharge conduit only through the gas release chamber, said supply conduit having a section smaller than a section of at least the end of the discharge conduit in communication with the cryogenic gas release chamber, so that said cryogenic gas is kept under pressure prior to being injected into said cryogenic gas release chamber, said supply conduit being internally delimited by an inner wall; and a source of cryogenic gas connected to said supply conduit and which provides said cryogenic gas to the end piece, wherein the metal tip of the end piece is adapted to freeze locally said human body area at a temperature lower than −50° C., wherein the flexible tube is a two-conduit extruded tube through which the supply conduit and the discharge conduit extend so as to define a continuity of material between said outer wall of the flexible tube and said inner wall of the supply conduit.

2. A cryogenic device according to claim 1, wherein said end of the flexible tube is made integral with said end piece and the cryogenic device further comprises a handle made of an insulating metallic material, the handle having a distal end provided with a thread cooperating with a nut provided on said end piece.

3. A cryogenic device according to claim 1, wherein the end piece is made integral with said end of the flexible tube by way of an adhesive.

4. A cryogenic device according to claim 3, wherein said end of the flexible tube inserted in the end piece is threaded so as to create a roughness at a gluing interface between the end piece and the flexible tube.

5. A cryogenic device according to claim 1, wherein a cross-section of said discharge conduit has substantially the shape of a crescent.

6. A cryogenic device according to claim 5, wherein the crescent has a concavity oriented towards said supply conduit.

7. A cryogenic device according to claim 1, wherein an end of the discharge conduit is bevelled.

8. A cryogenic device according to claim 1, wherein the flexible tube further includes a gas injection nozzle connected to the supply conduit and opening into said gas release chamber in the direction of the metal tip.

9. A cryogenic device according to claim 8, wherein the gas injection nozzle is inserted into the supply conduit.

10. A cryogenic device according to claim 8, wherein the gas injection nozzle has a conical injection tip.

11. A cryogenic device according to claim 1, wherein the cryogenic device includes an isolation sleeve covering a portion of the end piece.

12. A cryogenic device according to claim 1, wherein the flexible tube has a length between 1.5 and 2.5 meters.

13. A cryogenic device according to claim 1, wherein the discharge conduit is connected to a silencer discharging gas towards the outside of said cryogenic device.

* * * * *